(12) United States Patent
Kim et al.

(10) Patent No.: US 8,133,722 B2
(45) Date of Patent: Mar. 13, 2012

(54) CELL CULTURE COMPARTMENT UNIT AND ARRAY INCLUDING THE SAME

(75) Inventors: Sanghee Kim, Daejeon (KR); Chul Am Kim, Seoul (KR); Chang-Geun Ahn, Daejeon (KR); Moon Youn Jung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 131 days.

(21) Appl. No.: 12/635,682

(22) Filed: Dec. 10, 2009

(65) Prior Publication Data

US 2010/0159580 A1 Jun. 24, 2010

(30) Foreign Application Priority Data

Dec. 22, 2008 (KR) .................. 10-2008-0131297

(51) Int. Cl.
*C12M 1/12* (2006.01)

(52) U.S. Cl. ............... 435/297.1; 435/287.1; 435/287.2; 435/287.3; 435/297.2

(58) Field of Classification Search .... 435/287.1–287.3, 435/297.1–297.3
See application file for complete search history.

(56) References Cited

U.S. PATENT DOCUMENTS

| | | | |
|---|---|---|---|
| 6,797,631 B2 | 9/2004 | Kim et al. | |
| 2005/0009004 A1* | 1/2005 | Xu et al. | 435/4 |
| 2005/0106708 A1 | 5/2005 | Xing et al. | |
| 2006/0166247 A1* | 7/2006 | Abbud-Antaki | 435/6 |
| 2006/0226739 A1* | 10/2006 | Sakai | 310/339 |
| 2007/0218554 A1* | 9/2007 | Miyake et al. | 435/395 |

FOREIGN PATENT DOCUMENTS

KR  1020050015477 A  2/2005
KR  1020060134264 A  12/2006

OTHER PUBLICATIONS

Rachael T. Richardson et al., "The effect of polypyrrole with incorporated neurotrophin-3 on the promotion of neurite outgrowth from auditory neurons", Biomaterials 28, 2007, pp. 513-523.
W.A. Little, "Possibility of Synthesizing an Organic Superconductor", Physical Review, Jun. 15, 1964, pp. A1416-A1424, vol. 134, No. 6A.

* cited by examiner

*Primary Examiner* — Michael Marcheschi
*Assistant Examiner* — Shanta G Doe

(57) ABSTRACT

Provided are a cell culture compartment unit and an array including the same. The cell culture compartment unit includes: a cell culture region and a bio material emission region including a cell culture fluid, which are separated with a porous membrane therebetween; a piezoelectric device on the porous membrane of the cell culture region; a thin layer for cell attachment being on the piezoelectric device and having at least one surface on which cells are attachable; and a first power supply applying a first electric field to the piezoelectric device.

17 Claims, 2 Drawing Sheets

CELL CULTURE COMPARTMENT UNIT AND ARRAY INCLUDING THE SAME

CROSS-REFERENCE TO RELATED APPLICATIONS

This U.S. non-provisional patent application claims priority under 35 U.S.C. §119 of Korean Patent Application No. 10-2008-0131297, filed on Dec. 22, 2008, the entire contents of which are hereby incorporated by reference.

BACKGROUND OF THE INVENTION

The present invention disclosed herein relates to a compartment unit for cell culture and stem cell differentiation and an array including the same.

Research for biological cell differentiation has received much attention recently. Especially, research for differentiation of a stem cell, which is in an undifferentiated and immature state, has received further attention.

A stem cell can be maintained without differentiating into a specific cell, but if necessary, it can be split and copied to be differentiated into all kinds of cells constituting a body such as nerve, blood, and cartilage.

If differentiation of a biological cell such as a stem cell can be accomplished, it is applicable to specific kinds of diseases and various fields. Therefore, its research has been continuously conducted so far.

In relation to one of currently progressing research, various biological materials such as a growth factor, hormone, and cytokine (which are biological factors necessary for differentiation induction) are directly put into a cell culture fluid.

Additionally, in relation to tissue engineering capable of transplanting a generated body tissue to a necessary body portion in vitro, bio materials necessary for cell proliferation are injected into a cell culture fluid periodically in order to help cells to proliferate to be a target tissue.

Based on a drug delivery system, introduced is a method of manipulating a scaffold after a bio material necessary for a tissue engineering scaffold is mounted for cell attachment. Additionally, introduced is a method for continuously emitting a bio material for a certain period after a bio material necessary for cell proliferation is mounted on a microcapsule or an emulsion and then is injected in a cell culture fluid.

However, typical research is mainly limited to cell differentiation using a culture fluid composition and a differentiation induction material. Additionally, a method of using mechanical stimulus besides a biochemical factor has been introduced and its efficiency is highly evaluated. However, according to the method of using mechanical stimulus, equipment for mechanical stimulus cannot measure a single cell level due to its size, and only can measure target cells constituting a cluster.

SUMMARY OF THE INVENTION

The present invention provides a multiplex cell culture compartment unit capable of proliferating cells and providing stimulus simultaneously, which can be connected to an external control module without difficulties.

The present invention also provides a method of independently controlling cell proliferation and stimulus supply.

The present invention also provides an array capable of monitoring effects that respectively different kinds of materials provide on a single cell by mounting respectively different bio materials at its bottom region.

Embodiments of the present invention provide cell culture compartment units including: a cell culture region and a bio material emission region including a cell culture fluid, which are separated with a porous membrane therebetween; a piezoelectric device on the porous membrane of the cell culture region; a thin layer for cell attachment being on the piezoelectric device and having at least one surface on which cells are attachable; and a first power supply applying a first electric field to the piezoelectric device.

In some embodiments, the first power supply is connected to the piezoelectric device in order to apply a first electric field.

In other embodiments, the culture fluid transfers into the cell culture region through the porous membrane and thus is provided to the cells.

In still other embodiments, as the first electric field is applied, a unidirectional tensile stimulus is delivered to the cells by the piezoelectric polymer layer.

In even other embodiments, the cell culture compartment units further include: a conducting electrode spaced apart from the porous membrane in a vertical direction and disposed within the bio material emission region; and a conducting polymer disposed at the end part of the conducting electrode close to the membrane and including a bio material.

In yet other embodiments, a second power supply applying a second electrode field to the conducting electrode in order to emit the bio material to the cell culture fluid and the bio material includes at least one of cytokine, a growth Factor, and hormone. The conducting electrode is a metal electrode including at least one of Au and Pt.

In further embodiments, the conducting polymer includes polypyrrole series or a blending polymer including polypyrrole of a predetermined ratio.

In still further embodiments, the cell culture compartment units further include a controller controlling an intensity of the first or second electric field or an applying time of the first or second electric field in order to adjust an emission amount of the bio material.

In even further embodiments, the first power supply and the second power supply are separately disposed outside the cell culture region and the bio material emission region. The piezoelectric device includes at least one of a single polymer including polyvinylidene fluoride (PVDF) and collagen, a composite polymer including PVDF/poly(d,l)lactide acid (PDLLA), PVDF/collagen, polyethylene glycol (PEG), and collagen/poly-DL-lactide (PDLL), and a ceramic material including zirconium titanate.

In yet further embodiments, the thin layer for cell attachment is a flexible polymer including one of polydimethylsiloxane (PDSM), polyvinyl alcohol (PVA), and PEG/ethylene vinyl acetate (EVA).

In yet further embodiments, the bio material for cell attachment includes at least one of lysine, collagen type I, collagen type II, and laminin. The bio material for cell attachment has a size with which one or two to three cells constitute a group and has a thickness of less than 1 μm.

In yet further embodiments, the cell culture compartment units further include an outer wall surrounding an outer of the bio material emission region. The outer wall has an opening at one part; and the porous membrane is detachable to the opening.

In yet further embodiments, the cell culture compartment units are arranged in plurality and constitute an array type.

In yet further embodiments, the cell culture compartment units are regularly or irregularly arranged.

In yet further embodiments, the cell culture compartment units include at least two respectively different bio materials.

Accordingly, different effects on a cell can be monitored using respectively different kinds of bio materials in one cell culture compartment array.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures.

DETAILED DESCRIPTION OF PREFERRED EMBODIMENTS

Hereinafter, exemplary embodiments of the present invention will be described in detail with reference to the accompanying drawings so that this disclosure will be thorough and complete, and will fully convey the scope of the present invention to those skilled in the art.

Figure 1:
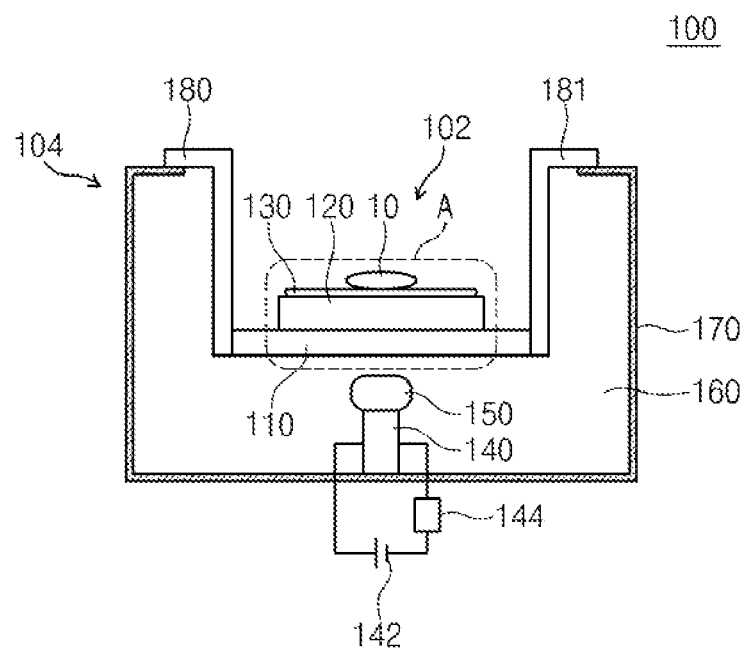
FIG. 1 is a sectional view illustrating a cell culture compartment unit according to an embodiment of the present invention.
Figure 2:
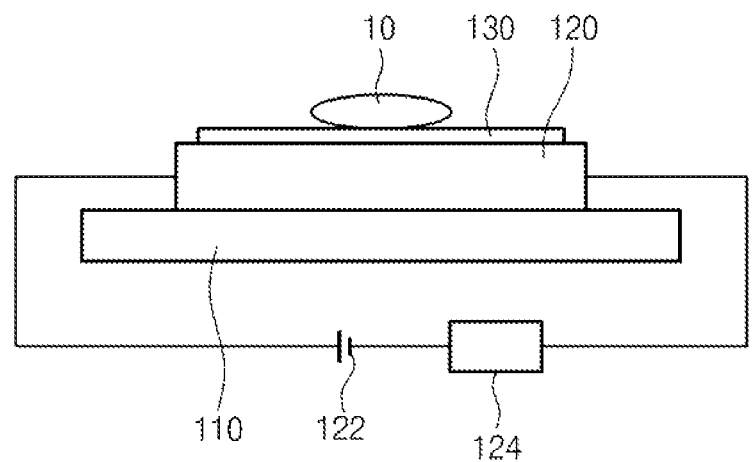
FIG. 2 is a sectional view illustrating a region A of a cell culture compartment unit of FIG. 1.

FIG. 1 is a sectional view illustrating a cell culture compartment unit according to an embodiment of the present invention. FIG. 2 is a sectional view illustrating the region A of the cell culture compartment unit of FIG. 1.

Referring to FIGS. 1 and 2, the cell culture compartment unit 100 includes a piezoelectric device 120, a thin layer for cell attachment 130, a first power supply 122, and a cell culture fluid 160. The cell culture compartment unit 100 is divided into a cell culture region 102 and a bio material emission region 104, with a porous membrane 110 therebetween.

The cell culture region 102 may include a target cell 10 to be cultured, and the bio material emission region 104 may include a cell culture fluid 160 and a bio material (not shown). The target cell 10 is cultured by supplying the cell culture fluid 160 and the bio material to the target cell 10.

The target cell 10 is to be cultured through the cell culture compartment unit 100 and also is a general biological cell such as a stem cell necessary for various experiments such as differentiation, proliferation, culture, and reaction for tension.

The porous membrane 110 is a layer where a plurality of pores are formed in its surface and inner part, and may serve as a sieve according to the size of a pore. If a pore has a predetermined size, a particle smaller than the predetermined size can penetrate into the layer without difficulties and a particle greater than the predetermined size cannot penetrate into the layer.

The piezoelectric device 120 is disposed on the porous membrane 110 of the cell culture region 102. The first power supply 122 for applying a first electric field (not shown) is connected to the piezoelectric device 120

A first controller 124 is connected to the first power supply 122. Since the first controller 124 controls the first power supply 122, an intensity of an electric filed applied to the piezoelectric device 120 or an electric field applying time can be adjusted. At this point, the first power supply 122 or the first controller 124 may be separately equipped outside the cell culture region 102 and the bio material emission region 104.

The thin layer for cell attachment 130 is disposed on the piezoelectric device 120 and has a surface on which the target cells 10 are attachable. As illustrated in the drawings, the target cell 10 is attached on the thin layer for cell attachment 130.

The piezoelectric device 120 is formed of a polymer that causes a piezoelectric effect. The piezoelectric device 120 utilizes the piezoelectric effect to provide tensile stimulus in a predetermined direction.

The piezoelectric effect is about relationship between a mechanical stress and electricity or voltage formation, and is a phenomenon when a mechanical stress is applied to a certain type of solid materials, polarization may occur proportional to the size of the mechanical stress, such that a voltage is generated or mechanical expansion and contraction occurs when a voltage is applied.

That is, according to a piezoelectric effect, when a mechanical stress is applied to a material such as quartz and topaz, an electric field is generated and its size is proportional to the applied stress degree. In a piezoelectric material, a voltage occurs generally because of a mechanical stress applied from the external. On the contrary, a form of a piezoelectric material may be modified through a voltage applied from the external. The piezoelectric material includes crystal, ceramic, and polymer material. The representative material includes a polymer material such as quartz ($SiO_2$), Zirconium Titanate, $BaTiO_3$, ceramic, and Polyvinylidene Fluoride.

According to the embodiment of the present invention, the piezoelectric device 120 may include a single polymer, a composite polymer, or a ceramic material. The single polymer includes PVDF and collagen. The composite polymer includes PVDF/PDLLA, PVDF/collagen, collagen/PEG, and collagen/PDLL. The ceramic material includes Zirconium Titanate.

Figure 3:
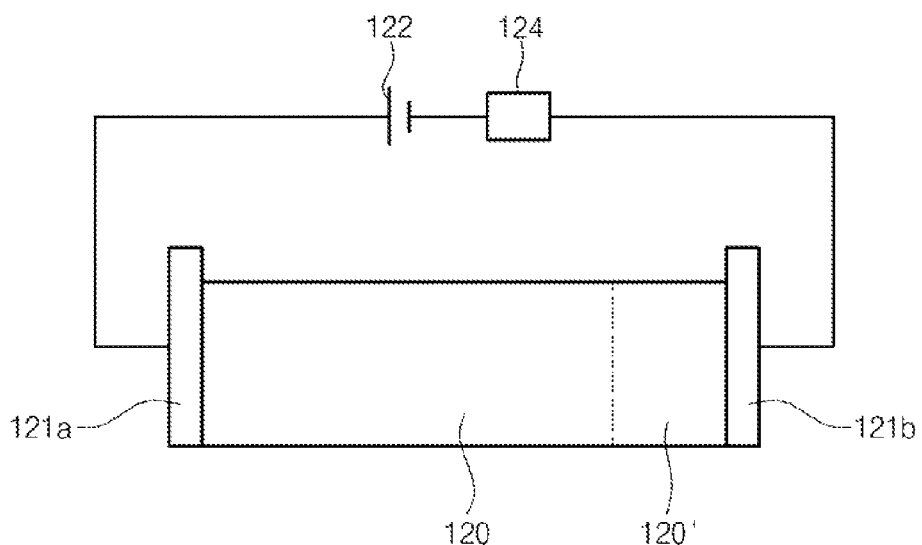
FIG. 3 is a sectional view illustrating a connection state of a piezoelectric device and a first power supply during applying of a voltage.

FIG. 3 is a sectional view illustrating a connection state of a piezoelectric device and a first power supply during applying of a voltage.

Referring to FIG. 3, the piezoelectric device 120 includes a first electrode 121a and a second electrode 121b, which directly contact the piezoelectric 120, at both sides. One of the first and second electrodes 121a and 121b is the cathode and the other one is the anode. Positions of the cathode and the anode may be interchangeable.

The first and second electrodes 121 and 121b are formed of a metal having a high conductivity such as gold (Au), silver (Ag), and platinum (Pt). The first and second electrodes 121a and 121b are connected to the first power supply 122. When the first power supply 122 is turned on, an electric field is generated between the first and second electrodes 121a and 121b. When the first power supply 122 is turned off, an electric field is not generated between the first and second electrodes 121a and 121b.

Once an electric field is generated between the first and second electrodes 121a and 121b because of a piezoelectric effect, the piezoelectric device 120 receives physical force and thus expands in a single direction. The extended portion is indicated with the reference number 120' in FIG. 3 for convenience of description. At this point, according to the embodiment of the present invention, the two electrodes 121a and 121b face each other in one direction. Accordingly, since an electric field is generated in one direction where the two electrodes 121*a* and 121*b* face each other, the piezoelectric device 120 expands in one direction where the electric field is generated.

The thin layer for cell attachment 130 is disposed on the piezoelectric device 120. Since the piezoelectric device 120 expands in one direction, tensile stimulus is applied to the target cell 10 through the thin layer for cell attachment 130. At this point, the thin layer for cell attachment 130 may have a thin thickness of about 1 μm in order to allow tensile stimulus occurring at the piezoelectric device 120 to be delivered to the target cell 10 to the maximum.

The thin layer for cell attachment 130 may have a size with which one or two to three cells constitute a group.

The thin layer for cell attachment 130 is formed of flexible polymer. The flexible polymer includes PDMS, PVA, and PEG/EVA.

Furthermore, the surface of the thin layer for cell attachment 130 may be additionally treated with a bio material (not shown) for cell attachment to allow cells to be easily attached to the surface. The bio material for cell attachment may be formed of a bio-friendly material to be easily attached on the surface. For example, the bio material for cell attachment includes lysine, collagen type I, collagen type II, and laminin.

The porous membrane 110 is formed on the bottom of the piezoelectric device 120, and the bio material emission region 104 is disposed on the bottom of the porous membrane 110.

The outlying of the bio material emission region 104 except for a region where the porous membrane 110 is formed is surrounded by the outer wall 170. That is, it has a box shape with a top open and the side of the outer wall 170 is bent toward the inner direction and then extends.

A fixing part 180 is connected to an end part of the porous membrane 110 to fix the porous membrane 110. The fixing part 180 may extend toward the bottom direction to allow the porous membrane 110 to be above the bio material emission region 104. The fixing part 180 may include a latch 181 to allow the fixing part 180 to be coupled and fixed to the outer wall 170, and the form of the latch 181 is not limited to a specific form. For example, if the latch 181 of the fixing part 180 is detachable, the porous membrane 110 can be replaced or modified if necessary.

The cell culture fluid 160 is disposed in the bio material emission region 104 surrounded by the outer wall 170. The cell culture fluid 160 transfers into the cell culture region 102 through the porous membrane 110. The cell culture fluid 160 sequentially soaks into the piezoelectric device 120 and the thin layer for cell attachment 130, and thus is provided to the target cell 10.

A conducting electrode 140 is disposed being spaced apart from the membrane 110 in a vertical direction of the membrane 110 within the bio material emission region 104. The conducting electrode 140 is vertically disposed from the base of the outer wall 170 toward the top direction. The conducting electrode 140 may be a metal electrode including gold (Au) or platinum (Pt).

A conducting polymer 150 containing a bio material is disposed on the conducting electrode 140.

The conducting polymer 150 may be formed of polyaniline series, polypyrrole series, or blending polymer containing polypyrrole series of a predetermined ratio. The conducting polymer 150 is polymer having electrical conductivity such as a metal.

In general, since polymer has a greater insulating property than a conducting property, it is usually used for wire coating. Research for a compound of the conducting polymer 150 has been extensively conducted after Little at Stanford University announced in 1964 that polymer having a conjugated backbone structure can be a super conductor at a room temperature.

The conducting polymer 150 has conductivity due to its quasi-continuous energy band. Generally, although electrons in atoms have a specific energy level, if a crystal lattice is formed due to coupling of atoms in the conducting polymer 150, atom positions in an orbit may vary. Additionally, due to interaction between atoms, energy levels of electrons are electrolyzed. The electrons having electrolyzed energy levels may generate a quasi-continuous energy band, and external electrons tied to one atom may freely move from other atoms. Accordingly, polyaniline or polypyrrole has a high electrical conductivity because external electrons freely move. Accordingly, it can be used as an electrode. Especially, in a case of polypyrrole, since its biocompatibility is excellent, it can be preferably used as an electrode material.

Since the conducting polymer 150 contains a bio material, the bio material is supplied to the target cell 10 and applies specific stimulus to the target cell 10. This bio material may vary according to types of stimulus applied to the target cell 10, but may include cytokine, a growth factor, and hormone.

The conductor electrode 150 is electrically connected to a second power supply 142, and it is determined whether the bio material is emitted or not according to on/off of the second power supply 142. That is, the second power supply 142 applies or does not apply an electric filed to the conducting electrode 140 according to on/off of the second power supply 142. If the second power supply 142 is turned on, a voltage is applied to the conducting electrode 140 and the conducting polymer 150. Therefore, an electric filed is generated and also electron's mobility improved. As the electron's mobility becomes active, the conducting polymer 150 changes into an expansion structure, and thus an internal bio material is emitted into the cell culture fluid 160. Since the size of the bio material is much less than that of pores of the porous membrane 110, the bio material moves to the upper part through the porous membrane 110 due to a natural convection phenomena in the cell culture fluid 160, and is provided to the target cell 10 through the same path as the cell culture fluid 160.

The second power supply 142 is connected to a second controller 144. Since the second controller 144 controls the second power supply 142, an intensity of an electric field and an electric field applying time can be adjusted to control an emission amount of the bio material. According to the emission amount of the bio material, a bio material concentration in the cell culture fluid 160 can be uniformly maintained.

At this point, the second power supply 142 or the second controller 144 can be equipped outside the cell culture region 102 and the bio material emission region 104. The second power supply 142 may be the same as the first power supply 122, but can be separately provided.

If the first and second power supplies 122 and 142 are separately provided, by separately controlling the intensities and applying times of an electric filed (which is applied to the piezoelectric device 120 and the conducting electrode 140), various culture conditions can be applied to the target cell 10. For example, cells can be cultured under the various conditions such as fixing of the type of a bio material and changing of tensile strength, fixing of the degree of tensile strength and changing of an emission amount and an emission time of a bio material, or changing of an emission amount and an emission time of a bio material and the degree of tensile strength.

The present invention includes a cell culture compartment array where a plurality of cell culture compartment units are arranged. FIG. 4 is a plan view illustrating a cell culture compartment array 200 according to an embodiment of the present invention. Here, the cell culture compartment units are indicated with only the outer wall 170, but its inside is the same as FIG. 1.

Figure 4:
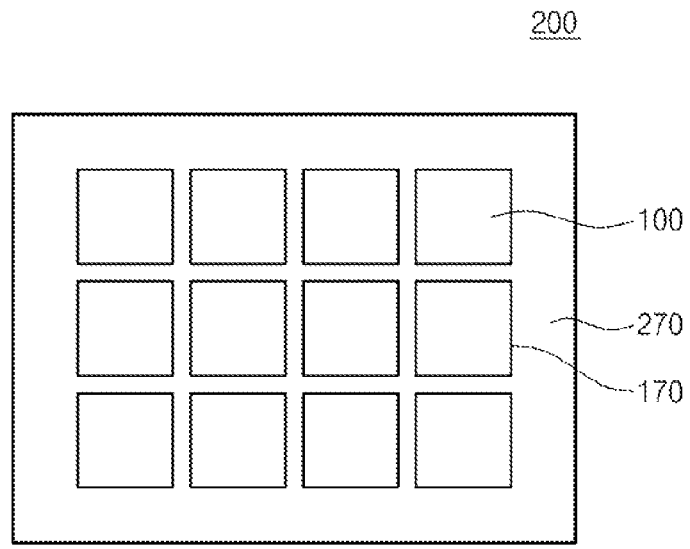
FIG. 4 is a plan view illustrating a cell culture compartment array according to an embodiment of the present invention.

Referring to FIGS. 1 and 4, according to the cell culture compartment array 200, cell culture compartment units 100 are regularly arranged on a substrate 270. At this point, the arrangement order of the cell culture compartment units 100 is not limited thereto, and thus can be randomly arranged if necessary. When the cell culture compartment units 100 are regularly arranged on the substrate 270, it may be in a matrix, for example.

The same target cells 10 may be cultured in the plurality of cell culture compartment units 100, but the present invention is not limited thereto. For example, two kinds of target cells 10 can be cultured if necessary, and the same number of types of target cells 10 as the cell culture compartment units 100 can be cultured.

Additionally, bio materials of the cell culture compartment units 100 may be the same or respectively different. For example, Cytokine may be used in one cell culture compartment unit, and a growth factor as a bio material may be used in another cell culture compartment unit. Accordingly, a bio material can be selectively mounted on each target cell 10, and the respectively different bio materials are simultaneously delivered to cells in order to monitor effects of respectively different bio materials. Consequently, a cell culture effect according to each bio material can be examined.

Furthermore, culture conditions of the plurality of cell culture compartment units 100 may be the same or respectively different. For example, by differently setting an electric field applying time and number of the first power supply 122 and the second power supply 142 applied to the each cell culture compartment unit 100, culture condition of each target cell 10 may vary. Accordingly, respectively different kinds of bio materials can be sequentially emitted according to a time necessary for each cell culture compartment.

If the above-mentioned cell culture compartment unit or cell culture compartment array is used, it is possible for cell culture to have a dimension of a single cell level during stem cell differentiation unlike conventional equipment. Accordingly, cell differentiation potential can be easily detected and thus, a very small amount of expensive biochemical differentiation material can be used.

As mentioned above, the present invention uses a property of a piezoelectric polymer having a form that is modified due to an electric field generated by an externally applied power supply and a property of a conducting polymer in which electron's mobility becomes active due to an electric field.

The present invention includes multiplex equipment that can simultaneously drive a single direction tensile stimulus application required for cell proliferation and stein cell differentiation and various kinds of bio material emissions. Especially, electrodes are respectively connected to the cell culture region at the upper part and the bio material emission region at the bottom part, such that a control system outside the equipment can be connected. Therefore, it is designed to diversely adjust an intensity and duration of an electricity applied to each electrode. Accordingly, by variously adjusting the supplying of tensile stimulus and bio material, cell culture conditions can be diversified, and as a result, cell culture can be easily performed under various conditions.

Moreover, since the porous membrane is connected to the fixing part and is detachable, it may be applied to various purposes such as cell proliferation and stem cell differentiation.

The cell culture compartment unit is designed to serve as an array, and respectively different kinds of bio materials are mounted on electrodes at the bottom. Therefore, it is possible to simultaneously monitor effects of various kinds of bio materials on a single cell.

According to the device of the present invention, cell culture fluid including a bio material is supplied and uniaxial tension is applied to a cell simultaneously. Therefore, the device can be used for both of cell proliferation for tissue engineering and stem cell differentiation The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A cell culture compartment unit comprising:
a cell culture region, and a biomaterial emission region including a cell culture fluid, which are separated with a porous membrane therebetween;
a piezoelectric device disposed over the porous membrane of the cell culture region;
a thin cell attachment layer disposed over the piezoelectric device and comprising at least one surface to which cells are attachable;
a first power supply configured to apply a first electric field to the piezoelectric device;
a conducting electrode spaced apart from the porous membrane in a vertical direction and disposed within the biomaterial emission region;
a conducting polymer including a biomaterial disposed between the conducting electrode and the membrane; and
a second power supply configured to apply a second electric field to the conducting electrode in order to emit the biomaterial into the cell culture fluid.

2. The cell culture compartment unit of claim 1, wherein the porous membrane is configured to transfer the cell culture fluid into the cell culture region, and the piezoelectric device is configured to deliver a unidirectional tensile stimulus to cells.

3. The cell culture compartment unit of claim 1, wherein the biomaterial comprises at least one of a cytokine, a growth factor, and a hormone.

4. The cell culture compartment unit of claim 1, wherein the conducting polymer comprises polypyrrole.

5. The cell culture compartment unit of claim 1, wherein the conducting electrode is a metal electrode including at least one of gold (Au) and platinum (Pt).

6. The cell culture compartment unit of claim 1, further comprising a controller configured to control an intensity of the first or second electric field, or a time for which the first or second field is applied, in order to adjust an emission amount of the biomaterial.

7. The cell culture compartment unit of claim 1, wherein the first power supply and the second power supply are separately disposed outside the cell culture region and the biomaterial emission region.

8. The cell culture compartment unit of claim 1, wherein the piezoelectric device comprises at least one of a single polymer including polyvinylidene fluoride (PVDF) and collagen, a composite polymer including PVDF/poly(d,l)lactide acid (PDLLA), PVDF/collagen, polyethylene glycol (PEG), and collagen/poly-DL-lactide (PDLL), and a ceramic material including zirconium titanate.

9. The cell culture compartment unit of claim 1, wherein the thin layer for cell attachment is a flexible polymer including one of polydimethylsiloxane (PDSM), polyvinyl alcohol (PVA), and PEG/ethylene vinyl acetate (EVA).

10. The cell culture compartment unit of claim 1, wherein a surface of the thin cell attachment layer is treated with a biomaterial for cell attachment.

11. The cell culture compartment unit of claim 10, wherein the biomaterial for cell attachment comprises at least one of lysine, collagen type I, collagen type II, and laminin.

12. The cell culture compartment unit of claim 1, wherein the thin layer for cell attachment is configured to attach a plurality of cells thereon, and has a thickness of less than 1 μm.

13. The cell culture compartment unit of claim 1, further comprising:
    an outer wall disposed to enclose the cell culture fluid; and
    an opening disposed in the outer wall,
    wherein the porous membrane is detachably coupled to the opening.

14. A cell culture compartment array comprising a plurality of arranged cell culture compartment units, each of the cell culture compartment units comprising:
    a cell culture region and a biomaterial emission region including a cell culture fluid, which are separated with a porous membrane therebetween;
    a piezoelectric device disposed over the porous membrane of the cell culture region;
    a thin layer disposed over the piezoelectric device and comprising at least one surface on which cells are attachable;
    a first power supply configured to apply a first electric field to the piezoelectric device;
    a conducting electrode spaced apart from the porous membrane in a vertical direction and disposed within the biomaterial emission region;
    a conducting polymer disposed at an end portion of the conducting electrode close to the membrane; and
    a second power supply configured to apply a second electric field to the conducting electrode.

15. The cell culture compartment array of claim 14, wherein the porous membrane is configured to transfer the cell culture fluid into the cell culture region, and the piezoelectric device is configured to deliver a unidirectional tensile stimulus to cells.

16. The cell culture compartment array of claim 14, wherein the cell culture compartment units comprise at least two respectively different biomaterials.

17. The cell culture compartment array of claim 14, further comprising a controller configured to control an intensity of the first or second electric field, or a time for which the first or second electric field is applied.

* * * * *